United States Patent [19]

Leffler et al.

[11] Patent Number: 4,464,360
[45] Date of Patent: Aug. 7, 1984

[54] GLYCOSPHINGALIPIDS FOR INHIBITING BACTERIAL ADHERENCE

[76] Inventors: Hakon Leffler, Änggårdsgatan 47; Catharina Svanborg Edén, Stora Gårda 29, both of Göteborg, Sweden

[21] Appl. No.: 336,345
[22] PCT Filed: May 8, 1981
[86] PCT No.: PCT/SE81/00138
§ 371 Date: Dec. 23, 1981
§ 102(e) Date: Dec. 23, 1981
[87] PCT Pub. No.: WO81/03175
PCT Pub. Date: Nov. 12, 1981

[30] Foreign Application Priority Data

May 9, 1980 [SE] Sweden .................................. 8003491
Jan. 23, 1981 [SE] Sweden .................................. 8100401
Jan. 23, 1981 [SE] Sweden .................................. 8100402

[51] Int. Cl.$^3$ ............................................. A61K 31/73
[52] U.S. Cl. ..................................... 424/180; 536/53; 536/55.1
[58] Field of Search ................ 424/180, 181; 536/123, 536/53, 55.1

[56] References Cited

U.S. PATENT DOCUMENTS 4,125,492 11/1978 Cautrecasas ........................ 536/1.1
4,182,757 1/1980 Tsujihara et al. .................... 424/180
4,238,473 12/1980 Lemieux et al. ..................... 424/180

FOREIGN PATENT DOCUMENTS 1910715 10/1969 Fed. Rep. of Germany ....... 536/1.1
2320760 3/1977 France ................................. 536/1.1

OTHER PUBLICATIONS

Chemical Abstracts, vol. 84, 1976, abstract No. 15602f, Biochemistry, 1975, 14, (22), 4837–41.
FEMS Microbiology Letters, vol. 5, 1979, G. Kallenius, R. Mollby, "Adhesion of *Escherichia coli* to Human Periurethral Cells Correlated to Mannose-Resistant Agglutination of Human Erythrocytes", pp. 295–299.
Glycoconjugate Research, Proceedings of the 4th International Symposium on Glycoconjugates, vol. 1, 1979, Ed. by J. D. Gregory and R. W. Jeanloz, (Academic Press, N.Y.–San Francisco–London), pp. 480–491.
Methods in Membrane Biology, vol. 2, 1974, Ed. by E. D. Korn, Plenum Press, N.Y.–London, P. A. Laine et al., "Isolation and Characterization of Membrane Glycosphinogolipids", pp. 205–244.
Chemical Abstracts, vol. 93, No. 17, issued 1980, Oct. 27, abstract No. 165835j, FEMS Microbiol. Letter, 1980, 8, (3), 127–34.
Euro. J. of Biochem., vol. 104, No. 2, issued 1980, Mar., Springer-Verlag, Berlin-Heidelberg-N.Y., A. Lundblad et al., "Release of Oligosaccharides from Human Erythrocyte Membranes of Different Blood-Group-P Phenotypes by Trifluoroacetolysis", pp. 323–330.
Proceedings of the National Academy of Sciences USA, vol. 73, No. 9, Sep. 1976, Washington, D. M. Marcus et al., "Abnormalities in the Glycosphingolipid Content of Human $P^k$ and p Erythrocytes", pp. 3263–3267.
Chemical Abstracts, vol. 52, 1958, 18581 a, Seitai no Kagaku, 6, 1955, 204–217.
Chemical Abstracts, vol. 85, 1976, abstract No. 92009r, J. Biochem., (Tokyo), 1976, 79, (6), 1253–61.
Chemical Abstracts, vol. 88, 1978, abstract No. 166344g, Proc. Natl. Acad. Sci. USA, 1978, 75, (2), 941–5.
Pathologie Biologie, vol. 26, No. 2, 1978, J. Delaunay, "Les Constituants De La Membrane Erythrocytaire", pp. 117–136, especially pp. 127–131.

*Primary Examiner*—Johnnie R. Brown
*Attorney, Agent, or Firm*—Brumbaugh, Graves, Donohue & Raymond

[57] ABSTRACT

Pharmaceutical preparations containing globotetraosylceramide, globotriaozylceramide or globotetraos, and the use of said preparations or compounds for treatment, prophylaxis or diagnosis of bacterial infections in the urinary tract. The compounds have the ability to inhibit the adherence of bacteria to human urinary tract epithelial cells.

2 Claims, No Drawings

GLYCOSPHINGALIPIDS FOR INHIBITING BACTERIAL ADHERENCE

DESCRIPTION

1. Technical Field

The present invention relates to compounds for use in medicine, and novel pharmaceutical preparations containing as active ingredient these compounds which are known per se. The pharmaceutical preparations are especially useful for inhibiting the adherence of bacteria to human urinary tract epithelial cells, and can be used for treatment, prophylaxis and diagnosis of urinary tract infections.

2. Background Art

Bacteria tend to grow attached to surfaces. Besides the general "stickiness" enabling bacteria to bind to almost any surface, host and tissue specific attachment of bacteria is known. Such specific attachment guides the distribution on mucous membranes, both of bacteria constituting the indigenous flora and of potential pathogens and is believed to be a prerequisite for susceptibility to infection of the host. For *Escherichia coli* isolated from patiens with urinary tract infection the severity of infection produced in vivo is strongly related to the capacity to adhere to human urinary tract epithelial cells in vitro.

The carbohydrate chains of glycosphingolipids are extremely variable, and are known to be involved in self- not self recognition as blood group antigens and receptors for bacterial toxins. Furthermore, the glycolipid pattern is species specific and differs between epithelial and non epithelial tissue. Carbohydrates at the cell surface have been implicated as possible receptors for attaching bacteria but no epithelial cell component interacting with bacteria has been identified. In connection with a recent observation (Svanborg Edén C, Leffler H. Scand. J. *Infect. Dis.* 1980, Suppl 24:144–147) that a fraction of glycolipids, isolated from human urinary tract epithelial cells, inhibited attachment of *E. coli* to cells from the same donor, a role for glycolipids as receptors for the attaching bacteria was suggested but no specific glycolipid had been identified before the date of our invention.

DISCLOSURE OF INVENTION

According to the present invention it has been found that the compounds globotetraosylceramide, globotriaosylceramide, and globotetraos have the ability to inhibit the adherence of bacteria to human urinary tract epithelial cells. Biological tests have indicated that this unexpected action is due to the fact that these compounds have the ability to attach to the cell walls of bacteria and thereby block some ligand function which is responsible for the adherence of bacteria to human urinary tract epithelial cells.

Urinary tract infections are commonly caused by an invasion of pathogenic bacteria, either from bacteria in the bowels or by bacteria invading through the urethra opening. The present invention provides pharmaceutical compositions having the ability to prevent adherence of potential pathogenic bacteria to human urinary tract epithelial cells, and thereby curing or preventing urinary tract infections.

More specifically, the invention relates to pharmaceutical preparations for inhibiting bacterial adherence to human urinary tract epithelial cells, which contain as active ingredient an effective amount of at least one of the compounds globotetraosylceramide of the formula

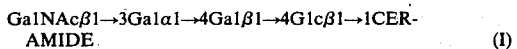
(I)

globotriaoxylceramide of the formula

(II)

and globotetraos of the formula

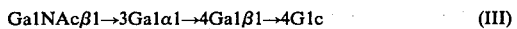
(III)

in association with a pharmaceutically acceptable carrier.

In a preferred embodiment the invention also relates to pharmaceutical preparations which contains solely globotetraosylceramide and/or globotriaosylceramide as an active ingredient. These preparations may as an additional ingredient contain an effective amount of the compound lactosylceramide of the formula.

(IV)

in proportions of 1:10 to 10:1 per weight of the ceramides of the formulas I and II. Lactosylceramide does not in itself possess any ability to inhibit bacterial adherence. However, most surprisingly it has been found to strongly potentiate the inhibitory effects of globotetraosylceramide and globotriaoxylceramide.

The active ingredients globotetraosylceramide, globotriaosylceramide, globotetraos and lactosylceramide are compounds known per se, which can be prepared according to known methods. These compounds have not previously been suggested to possess any medical use.

The active ingredients may according to the invention be formulated for use in human medicine for therapeutic prophylactic or diagnostic use. In clinical practice the active ingredients will normally be administered topically, orally, or by rectal administration, in the form of a pharmaceutical preparation comprising the active ingredients, in association with a pharmaceutically acceptable carrier which may be a solid, semi-solid or liquid diluent or an ingestible capsule, and such preparations comprise a further aspect of the invention. The compounds may also be used without carrier material. As examples of pharmaceutical preparations may be mentioned tablets, drops, suppositories, preparations for topical application such as ointments, jellies, creams, powders, drops and suspensions. Usually the active substance will comprise from 0.05 to 99% by weight of the preparation, for example from 0.1 to 50% for preparations intended for oral administration and from 0.5 to 80% for preparations intended for topical administration. For topical application, especially for application to the urethra opening, the preparations are suitably in the form of an ointment, gel, suspension, or cream. The amount of active substance may vary, for example from 0.5–80% by weight of the active substance. Such preparations for topical application may be prepared in known manner by mixing the active substance with known carrier materials such as isopropanol, glycerol, paraffin, stearyl alcohol, and polyethylene glycol.

To produce pharmaceutical preparations in the form of dosage units for oral application containing a compound of the invention, the active ingredients may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine and also may include lubricants such as magnesium or calcium stearate or a Carbowax or other polyethylene glycol waxes compressed to form tablets or cores for dragées. If dragées are required, the cores may be coated for example with concentrated sugar solutions which may contain gum arabic, talc and/or titanium dioxide, or alternatively with a film forming agent dissolved in easily volatile organic solvents or mixtures of organic solvents. Dyestuffs can be added to these coatings, for example, to distinguish between different contents of active substance. For the preparation of soft gelatine capsules consisting of gelatine and, for example, glycerol as a plasticizer, or similar closed capsules, the active substance may be admixed with a Carbowax or a suitable oil as e.g. sesame oil, olive oil, or arachis oil. Hard gelatine capsules may contain granulates of the active substance with solid, pulverulent carriers such as lactose, saccharose, sorbitol, mannitol, starches (for example potato starch, corn starch or amylopectin), cellulose derivatives or gelatine, and may also include magnesium stearate or stearic acid as lubricants.

By using several layers of the active drug, separated by slowly dissolving coatings sustained release tablets are obtained. Another way of preparing sustained release tablets is to divide the dose of the active drug into granules with coatings of different thicknesses and compress the granules into tablets together with the carrier substance. The active substance can also be incorporated in slowly dissolving tablets made for instance of fat and wax substances or evenly distributed in a tablet of an insoluble substance such as a physiologically inert plastic substance.

In order to obtain dosage units of oral preparations—tablets and capsules—which are designed so as to prevent release of and possible decomposition of the active substance in the gastric juice, the tablets and dragées may be enteric-coated, that is provided with a layer of a gastric juice-resistant enteric film or coating having such properties that it is not dissolved at the acidic pH in the gastric juice. Thus, the active substance will not be released until the preparation reaches the intestines. As examples of such known enteric coatings may be mentioned cellulose acetate phthalate, hydroxypropylmethylcellulose phthalates such as those sold under the trade names HP 55 and HP 50, and Eudragit L and Eudragit S.

Effervescent powder may be prepared by mixing the active ingredient with non-toxic carbonates or hydrogen carbonates of e.g. sodium, potassium or calcium, such as calcium carbonate, potassium carbonate and potassium hydrogen carbonate, and solid, non-toxic acids such as tartaric acid, ascorbic acid, and citric acid, and for example aroma.

Liquid preparations for oral application may be in the form of elixirs, syrups or suspensions, for example solutions containing from 0.1% to 20% by weight of active substance, sugar and a mixture or ethanol, water, glycerol, propylene glycol and optionally aroma, saccharine and/or carboxymethylcellulose as a dispersing agent.

The dosage at which the active ingredients are administered may vary within a wide range and will depend on various factors such as for example the severity of the infection, the age and weight of the patient, and may have to be individually adjusted. As a possible range for the amount of active ingredients which may be administered per day may be mentioned from 0.1 mg to 2000 mg or from 1 mg to 2000 mg.

The pharmaceutical compositions containing the active ingredients may suitably be formulated so that they provide doses within these ranges either as single dosage units or as multiple dosage units.

Thus, it has been found according to the present invention that globotetraosylceramide, globotriaocylseramide and globotetraos have the ability to inhibit the adherence of bacteria to human urinary tract epithelial cells. Since such an adherence in many cases is an essential prerequisite for susceptibility to urinary tract pathogenic bacteria, the above active ingredients and corresponding pharmaceutical preparations are useful in therapeutic and/or prophylactic treatment of urinary tract infections.

BEST MODE OF CARRYING OUT THE INVENTION

The preferred aspect of the invention is the use of globotetraosylceramide in the treatment of urinary tract infections caused by *E. coli*.

BIOLOGICAL TESTS

Adhesion inhibition by glycolipids: The in vitro test system for bacterial adhesion to urinary tract epithelial cells has been described in Infect. Immun. 18, 767–774 (1977). The cells were collected from the sediment of freshly voided urine from one healthy donor, and consisted of about 80 percent squamous and 20 percent transitional epithelial cells. An *E. coli* 3669 strain (02 K nontypable), isolated from the urine of a girl with acute pyelonephritis was used. The strain attached to human but not to rat urinary tract epithelial cells and agglutinated human but not guinea pig erythrocytes. For testing, bacteria were cultivated in Luria broth for 16 h, sedimented by centrifugation and resuspended in phosphate-buffered saline, PBS (pH 7.1, 300 mOsm per 1). To $10^8$ bacteria were added $10^5$ urinary tract epithelial cells. After incubation for 60 min at 37° C. the mixture was washed free of unattached bacteria, and the number of bacteria on the epithelial cells counted by light microscopy. Adhesion is given as the mean number of bacteria attached to 40 epithelial cells.

For inhibition experiments samples of the different glycolipids to be tested were taken from solutions in chloroform-methanol 2:1. The solvent was removed by evaporation in a stream of nitrogen followed by suction in an exsiccator over night. After addition of 0.5 or 1.0 ml of 0.85 percent of NaCl or PBS the samples were sonicated in a water bath for 30–60 seconds to give a glycolipid suspension. Bacteria were preincubated with glycolipid suspension ($10^8$ bacteria in 100 μl and 0.5 ml of glycolipid) for 30 min. After addition of $10^5$ urinary sediment epithelial cells adhesion testing was continued as described above.

The glycolipids to be tested were prepared in the laboratory of K-A Karlsson, Institute of Medical Biochemistry, Göteborg, Sweden. The known structures (Laine, R. A., Stellner, K. and Hakomori, S.-i. (1974) in Methods in Membrane Biology (Korn, E. D. ed) vol. 2, pp. 205-244, Plenum Press, New York) were confirmed by mass spectrometry, NMR spectroscopy and degradative methods.

Thus, lactosylceramide was purified from human brain and globotriaosylceramide and globotetraosylceramide from human erythrocytes. For the preparation of lactoneotetraosylceramide, the major ganglioside of human erythrocytes, N-Acetylneuraminosyllactoneotetraosylceramide, was isolated and degraded by *Vibrio cholera* neuraminidase Calbiochem. (San Diego, USA)

The results from the tests are depicted in Tables 1 and 2 below.

The globotetraosylceramide was found to be the most effective inhibitor of the bacterial attachment while globotriaosylceramide also had some inhibitory activity (Table 1 and 2). The other glycolipids tested were not inhibitory (Table 1). Also, some combinations of pure glycolipids were tested. Thus, it was found that lower amounts of globotetraosylceramide were needed for inhibition of adhesion when a glycosphingolipid in itself not affecting attachment viz. lactosylceramide in an amount of 100 μg was added together with globotetraosylceramide (Table 2).

TABLE 1

| Preincubated with | μg in 0.5 ml | No. bacteria adhering per cell, % of control |
|---|---|---|
| Lactosylceramide | 100 | 104 |
| Globotriaosylceramide | 150 | 55 |
| Globotetraosylceramide | 100 | 20 |
| Lactoneotetraosylceramide | 100 | 100 |

TABLE 2

Inhibition of bacterial attachment by globotetraosylceramide and globotriaosylceramide presented in different forms. Average number of bacteria adhering per cell, % of control.

| Amount (μg in 0.5 ml) | Globotetraosylceramide | Globotriaosylceramide | With addition of lactosylceramide[a] | |
|---|---|---|---|---|
| | | | Globotetraosylceramide | Globotriaosylceramide |
| 400 | 9 | 61 | 2 | 24 |
| 200 | 4 | 54 | 11 | 75 |
| 100 | 20 | — | 12 | 59 |
| 40 | 61 | 67 | 12 | 59 |
| 20 | 86 | — | 41 | — |
| 10 | 99 | — | 86 | — |

[a]200 μg of lactosylceramide were added to the 400 μg sample of globotetra-globotriaosylceramide and 100 μg was added to the other samples.

The inhibitory effects of globotetraosylceramide has been confirmed by tests with other *E. coli* strains attaching to human urogenital epithelial cells. In a still further test it has been shown that 90% out of a large sample of pyelonephritis *E. coli* strains which attach to human urogenital epithelial cells also do bind to globotetraosylceramide.

ADHESION INHIBITION BY THE TETRASACCHARIDE GLOBOTETRAOS

In a further series of tests it has been shown that globotetraos, viz. the free tetrasaccharide residue of globotetraosylceramide also can inhibit the adhesion of pyelonefritis *E. coli* to uroepithelial cells. The test were made in accordance with the general procedure described above, using the strain *E. coli* 36692. Bacteria ($10^8$/ml) were mixed with globotetraos (~150 μg/ml) or PBS and then incubated for 30 min at 37° C. Epithelial cells (human and mouse) were then added and after incubation the number of bacteria on the cells were counted as described above.

The results are depicted in Table 3 below. The globotetraos was obtained by ozonolysis according to Wiegandt and Baschang (1965) using globotetraosylceramide obtained from human erythrocytes.

TABLE 3

| | Adhesion (% of saline control) | |
|---|---|---|
| Bacteria preincubated with | Human cells | Mouse cells |
| Phosphatebuffer, PBS | 100 | 100 |
| Globotetraos | 27 | 15 |

Protection against ascending urinary tract infection in mice with globotetraos. The strain *E. coli* 36692, originally isolated from urine of a patient with pyelonephritis, was used for testing. The strain was adhesive to human urinary tract epithelical cells by recognizing globotetraosylceramide as receptor (Leffler, H., and Svanborg Edén, C. 1980. Chemical identification of a glycosphingolipid receptor for *Escherichia coli* attaching to human urinary tract epithelial cells and agglutinating human erythrocytes. FEMS Microbiol. Lett. 8:127). It has now been shown that this strain also adheres to uroepithelial cells of mice and that it gives experimental pyelonephritis (bacteria in the kidney) when injected in the bladder of mice.

In the tests *E. coli* 36692 were preincubated with globotetraos or phosphatebuffer for 30 min at 37° C. The adhesion to mouse bladder epithelial cells of the two samples was compared in vitro, before injection of 0.05 ml into the bladder of mice. Ten animals were used in each group. After sacrifice of the animals two hours after injection cultures were performed on kidneys, bladders and urine.

The results are given in Table 4 below. In the first (A) series of test the injected bacterial suspension contained $10^8$ bacteria/ml, and the preincubation was made with a solution containing 200 μg/ml of globotetraos. In the second (B) series of test the bacterial suspension contained $2.10^9$ bacteria/ml, and the preincubation was made with a solution containing about 150 μg/ml of globotetraos.

TABLE 4

| Bacteria pretreated with | | No. of positive cultures | | | No. dead |
|---|---|---|---|---|---|
| | | Kidney | Bladder | Urine | |
| phosphatebuffer | (A) | 10 | 8 | 9 | 0 |
| globotetraos | (A) | 0 | 7 | 10 | 0 |
| phosphatebuffer | (B) | 9 | 8 | 7 | 5 |
| globotetraos | (B) | 6 | 2 | 3 | 0 |

It is seen from the results in the table that, firstly, with a low dose (A) of pretreated bacteria the tendency for pyelonephritis (bacteria in the kidney) is eliminated. Secondly, with a higher bacterial dose (B) the survival of mouse is increased from 5 to 10 when using globotetraos pretreated bacteria. These beneficial results have been confirmed in tests with other bacteria and with a larger number of animal tests.

DISCUSSION

In a previous study (Svanborg Edén, C., Hansson, L. Å., Jodal, U., Lindberg, U., and Sohl Åkerlund, A. 1976. Variable adhesion to normal urinary tract epithelial cells of *Escherichia coli* strains associated with various forms of urinary tract infection. Lancet II:490) it has been shown that at least 70% of *E. coli* strains isolated from pyelonephritis patients are adhesive to urinary tract epithelial cells. This indicates a general therapeutic usefulness of agents interfering with this adhesion, such as the compounds tested above.

The therapeutic effect of interference with adhesion is dependent on whether adhesion is a descisive event in the infectious process or not. Two lines of evidence indicate that this is the case. Firstly, adhesive capability is common among pyelonephritis *E. coli* and rare among normal faecal *E. coli* (Lancet, II:490 (1976). Secondly, people with a decreased capacity to synthesize glycolipid receptors (as measured by bloodgroup) has been shown to run a lower risk of attracting urinary tract infection (Lancet, 1981).

DIAGNOSTIC USE

The characteristics of a bacterial strain to recognize a receptor, such as globotetraosylceramide (globoside), globotriaosylceramide, or globotetraos may be demonstrated by using particles or surfaces with adfixed receptor.

The particles may be erythrocytes coated with receptor as in Leffler, H. and Svanborg Edén, C., (1980) FEMS Microbiol. Letters 8, 127-134. Also possibly useful are synthetic particles or surfaces with bound glycolipid, for example covalently bound to agarose or glass beads. (The Journal of Biological Chemistry, Vol. 249, No. 14, 4460-4466 (1974)). polystyrene tubes, microtiter plates and similar. Linkage to or coating of other materials such as latex is also possible.

The bacterial property is demonstrated by agglutination of particles after addition of bacteria, or visualization of bacterial binding to a surface. If agglutination occurs for particles with receptor but not particles without receptor recognition of the receptor by bacteria is demonstrated.

PHARMACEUTICAL PREPARATIONS

The following Examples illustrate the preparation of pharmaceutical preparations of the invention.

EXAMPLE 1

Ointment I

| | |
|---|---|
| Globotetraosylceramide | 2.5 g |
| Cetyltrimethylammonium bromide | 0.6 g |
| Stearyl alcohol | 2.25 g |
| Cetanol | 6.75 g |
| Liquid paraffin | 17.0 g |
| Glycerol | 12.0 g |
| Hydrochloric acid to pH 6.5 | |
| Distilled water | ad 100.0 g |

EXAMPLE 2

Ointment II

| | |
|---|---|
| Globotriaosylceramide | 2.5 g |
| Polyethylene glycol 1500 | 50 g |
| Polyethylene glycol 4000 | 15 g |
| Propylene glycol | ad 100 g |

EXAMPLE 3

Ointment III

| | |
|---|---|
| Globotetraosylceramide | 2.0 g |
| Lactosylceramide | 1.0 g |
| Sorbitan monoleate | 5.0 g |
| Petrolatum | ad 100 g |

EXAMPLE 4

Ointment IV

| | |
|---|---|
| Globotetraos | 2.5 g |
| Polyethylene glycol 1500 | 50 g |
| Polyethylene glycol 4000 | 15 g |
| Propylene glycol | ad 100 g |

EXAMPLE 5

Jelly

| | |
|---|---|
| Globotetraosylceramide | 4.0 g |
| Methocel | 4.0 g |
| Methyl paraoxybenzoate | 0.12 g |
| Propyl paraoxybenzoate | 0.05 g |
| Sodium hydroxide and hydrochloric acid to pH 6.7 | |
| Distilled Water | ad 100.0 ml |

EXAMPLE 6

Solution for topical use

| | |
|---|---|
| Globotetraosylceramide | 2.00 g |
| Isopropanol | 38.0 g |
| Glycerol | 13.6 g |
| Hydrochloric acid to pH 5.0-7.0 | |
| Purified water | ad 100.0 g |

EXAMPLE 7

Drops

| | |
|---|---|
| Globotetraosylceramide | 2.00 g |
| Ascorbic acid | 1.00 g |
| Sodium pyrosulfite | 0.10 g |
| Disodium edetate | 0.10 g |
| Liquid glucose | 50.00 g |
| Absolute alcohol | 10.00 g |
| Purified water | ad 100.00 ml |

EXAMPLE 8

Drops

| | |
|---|---|
| Globotetraosylceramide | 1.00 g |
| Lactosylceramide | 1.00 g |
| Citric acid | 1.00 g |
| Disodium edetate | 0.10 g |
| Liquid glucose | 50.00 g |
| Ethanol 95% | 10.00 g |
| Sodium hydroxide and hydrochloric acid to pH 6.2-6.8 | |
| Purified water | ad 100.0 ml |

EXAMPLE 9

Tablets

| | |
|---|---|
| Each tablet contains | |
| Globotetraosylceramide | 20.0 mg |
| Maize starch | 25.0 mg |
| Lactose | 190.0 mg |
| Gelatin | 1.5 mg |
| Talc | 12.0 mg |
| Magnesium stearate | 1.5 mg |

250.0 mg

EXAMPLE 10

Gastric juice-resistant tablets

Tablets according to Example 8 are coated with an enteric coating solution with the following composition:

| | |
|---|---|
| Cellulose acetate phtalate | 120.0 g |
| Propylene glycol | 30.0 g |
| Sorbitan monoleate | 10.0 g |
| Ethanol 95% | 450.0 ml |
| Acetone | q.s. ad 1000.0 ml |

The coating is carried out by a pouring procedure in a conventional coating pan or by spraying the tablets in a pan spray tablet coater.

EXAMPLE 11

Suppositories

Each suppository contains:

| | |
|---|---|
| Globotetraosylceramide | 20.0 mg |
| Ascorbyl palmitate | 1.0 mg |
| Suppository base (Imhausen H or Witepsol H) | ad 2000.0 mg |

EXAMPLE 12

Syrup

| | |
|---|---|
| Globotetraosylceramide | 0.200 g |
| Liquid glucose | 30.0 g |
| Sucrose | 50.0 g |
| Ascorbic acid | 0.1 g |
| Sodium pyrosulfite | 0.01 g |
| Disodium edetate | 0.01 g |
| Orange essence | 0.025 g |
| Certified colour | 0.015 g |
| Purified water | ad 100.0 g |

EXAMPLE 13

Syrup

| | |
|---|---|
| Globotriaosylceramide | 0.200 g |
| Liquid glucose | 30.0 g |
| Sucrose | 50.0 g |
| Ascorbic acid | 0.1 g |
| Disodium edetate | 0.01 g |
| Orange essence with solubilizer | 0.25 g |
| Hydrochloric acid to pH 6.0–6.5 | |
| Purified water | ad 100.0 g |

We claim:

1. A method of treating mammals suffering from infection due to bacteria adhering to the epithelial cells of the urinary tract comprising administering an amount of at least one of an active compound selected from the group consisting of globotetraosylceramide, globotriaoxylceramide and globotetraos effective to treat the bacterial infection.

2. A method of treating mammals suffering from infection due to bacteria adhering to the epithelial cells of the urinary tract comprising administering an amount of at least one of an active compound selected from the group consisting of globotetraosylceramide and globotriaosylceramide effective to treat the bacterial infection, together with lactosylceramide in proportions of 1:10 to 10:1 per weight of globotetraosylceramide or globotriaosylceramide.

* * * * *